US012187677B2

United States Patent
Sawyer et al.

(10) Patent No.: US 12,187,677 B2
(45) Date of Patent: Jan. 7, 2025

(54) PROCESS FOR THE REMOVAL OF CARBON MONOXIDE FROM NON-CATALYTIC OXIDATIVE DEHYDROGENATION PRODUCT STREAMS

(71) Applicant: EcoCatalytic Inc., Weston, MA (US)

(72) Inventors: Gary A. Sawyer, Media, PA (US); C. Andrew Jones, Newtown Square, PA (US); John A. Sofranko, Weston, MA (US)

(73) Assignee: EcoCatalytic Inc., Weston, MA (US)

( * ) Notice: Subject to any disclaimer, the term of this patent is extended or adjusted under 35 U.S.C. 154(b) by 0 days.

(21) Appl. No.: 18/212,999

(22) Filed: Jun. 22, 2023

(65) Prior Publication Data

US 2023/0331646 A1 Oct. 19, 2023

Related U.S. Application Data

(62) Division of application No. 17/871,575, filed on Jul. 22, 2022, now Pat. No. 11,767,276.

(Continued)

(51) Int. Cl.
*C07C 7/148* (2006.01)
*B01J 21/02* (2006.01)
(Continued)

(52) U.S. Cl.
CPC .......... *C07C 7/14816* (2013.01); *B01J 21/02* (2013.01); *B01J 27/053* (2013.01);
(Continued)

(58) Field of Classification Search
CPC ......... C07C 7/14816; C07C 2/82; C07C 5/48; B01J 21/02; B01J 27/053; B01J 27/1806;
(Continued)

(56) References Cited

U.S. PATENT DOCUMENTS 6,475,454 B1  11/2002  Cole et al.
10,138,182 B2  11/2018  Sofranko et al.
(Continued)

FOREIGN PATENT DOCUMENTS

WO  2020141395 A1  7/2020

OTHER PUBLICATIONS

Chowdhury et al., "Chem CAD Simulation of Benfield Process to Remove CO2 from Natural Gas and Inspection of Temperature Profile of Key Units", Advances in Mechanical Engineering and its Application (AMEA), 2013, vol. 3, No. 2, pp. 299-303.

(Continued)

*Primary Examiner* — Ali Z Fadhel
(74) *Attorney, Agent, or Firm* — Buchanan Ingersoll & Rooney PC

(57) ABSTRACT

A method of removing CO from a mixture of CO and saturated or unsaturated hydrocarbons is provided. In one embodiment, the method is to contact a feed stream with an oxygen transfer agent; and then oxidize at least a portion of the CO to $CO_2$ to produce a stream enriched in $CO_2$. The saturated and unsaturated hydrocarbons in the feed are not further oxidized during the oxidation. The oxygen transfer agent includes at least one of: i) water; ii) at least one reducible metal oxide; iii) at least one reducible chalcogen; or mixtures thereof. In another embodiment, the CO is converted to methane. The unsaturated hydrocarbons in the feed are not hydrogenated. In both of these alternatives, the $CO_2$ or methane are then removed. Systems for removing the CO are also provided.

14 Claims, 4 Drawing Sheets

Related U.S. Application Data

(60) Provisional application No. 63/224,880, filed on Jul. 23, 2021.

(51) Int. Cl.
| | |
|---|---|
| *B01J 27/053* | (2006.01) |
| *B01J 27/18* | (2006.01) |
| *C01B 3/12* | (2006.01) |
| *C01B 3/48* | (2006.01) |
| *C01B 3/58* | (2006.01) |
| *C01B 32/50* | (2017.01) |
| *C07C 2/82* | (2006.01) |
| *C07C 5/48* | (2006.01) |

(52) U.S. Cl.
CPC ............ *B01J 27/1806* (2013.01); *C01B 3/12* (2013.01); *C01B 3/48* (2013.01); *C01B 32/50* (2017.08); *C07C 2/82* (2013.01); *C07C 5/48* (2013.01); *C01B 3/583* (2013.01); *C01B 2203/044* (2013.01)

(58) Field of Classification Search
CPC .. C01B 3/12; C01B 3/48; C01B 32/50; C01B 3/583; C01B 2203/044
See application file for complete search history.

(56) References Cited

U.S. PATENT DOCUMENTS

| | | | |
|---|---|---|---|
| 10,919,027 | B1 | 2/2021 | Sofranko et al. |
| 10,968,149 | B2 | 4/2021 | Sofranko et al. |
| 11,046,892 | B1 | 6/2021 | Sofranko et al. |
| 11,104,625 | B1 | 8/2021 | Sofranko |
| 11,192,092 | B1 | 12/2021 | Sofranko |
| 2007/0083073 | A1* | 4/2007 | Bagherzadeh ............ C01B 3/48 502/340 |
| 2013/0131380 | A1 | 5/2013 | Dubois et al. |
| 2020/0223768 | A1 | 7/2020 | Van Rossum et al. |
| 2020/0407289 | A1 | 12/2020 | Simanzhenkov et al. |
| 2022/0144722 | A1* | 5/2022 | Goodarznia .............. C07C 1/24 |

OTHER PUBLICATIONS

Shimekit et al., "Natural Gas Purification Technologies - Major Advances for CO2 Separation and Future Directions", Advances in Natural Gas Technology, 2012, 37 pages.

Subramani et al., "Water Gas Shift Reaction", ScienceDirect Topics, https://www.sciencedirect.com/topics/engineering/water-gas-shift-reaction, 2021, 11 pages.

Zimmermann et al., "Ethylene", Ullmann's Encyclopedia of Industrial Chemistry, 2012, vol. 13, 66 pages.

Entire patent prosecution history of U.S. Appl. No. 17/871,575, filed Jul. 22, 2022, entitled, "Oxidative Process for the Removal of Carbon Monoxide From Non-Catalytic Oxidative Dehydrogenation Product Streams."

\* cited by examiner

PROCESS FOR THE REMOVAL OF CARBON MONOXIDE FROM NON-CATALYTIC OXIDATIVE DEHYDROGENATION PRODUCT STREAMS

CROSS REFERENCE TO RELATED APPLICATIONS

This application is a Divisional of U.S. application Ser. No. 17/871,575, filed Jul. 22, 2022, which claims the benefit of and priority from U.S. Provisional Application No. 63/224,880, filed on Jul. 23, 2021, the disclosure of each of which are incorporated by reference herein in their entireties for all purposes.

TECHNICAL FIELD

The present disclosure is related to systems and methods for the efficient removal of by-product carbon monoxide from oxidative dehydrogenation processes.

BACKGROUND

Ethylene and propylene are important building blocks for the petrochemical industry. These olefins are used in the manufacturing of polymers such as polyethylene, polypropylene, polystyrene and many more chemicals of commercial interest. Over 90% of the global olefin production comes from the high temperature steam cracking of naphtha or ethane and propane. The steam cracking process, which utilizes furnaces, is highly energy intensive, and 1.5 to 2 tons of carbon dioxide is produced for every ton of olefin product produced.

Natural gas production from shale deposits has dramatically increased supply of methane, ethane and propane in recent years. As a result of the continued global demand for olefins and the potential for a new growing supply of ethane and propane available in natural gas liquids from shale deposits, a significant amount of interest and investment is currently centered around expanding the production capacity of ethylene and propylene derived from these new sources. Numerous olefin grass root and expansion projects are either under contract or in the planning stages to take advantage of the relative low cost liquids from wet shale gas. The supply of natural gas in the US has increased dramatically in recent years as has the co-production of shale oil. Natural gas is often produced as a mixture of methane and hydrocarbons such as ethane, propane and butanes. This so called "wet gas" often contains greater than 20% by volume of heavier components. To feed conventional ethane steam cracking furnaces, capital and energy intensive equipment is used to separate these gas components so that primarily ethane, or ethane/propane, mixtures are fed to the steam crackers. However, there are many environmental and cost challenges to bringing on this level of new capacity of steam crackers.

Olefin production is the largest emitter of $CO_2$ and NOx in the organic chemical industry. With worldwide per year of $CO_2$ and roughly 1.4 MT/year of NOx. Projects located in severe EPA non-attainment zones are challenged by the increase cost of NOx control. The total greenhouse gas (GHG) emission profile, reported in $CO_2$ equivalents, is another critical part of the permitting for all production expansions.

The industry continues to push for production technology that: (1) generates higher overall yield of ethylene and propylene; (2) increases the run length between furnace turnarounds (e.g. inspections, repairs, improvements, etc.); (3) lowers steam and energy utilization; (4) lowers all GHGs including carbon dioxide and NOx.

Oxidative dehydrogenation (ODH) of ethane and propane offers a potential solution for these needs provides an opportunity to improve the efficiency of olefin production. The oxidative coupling of methane (OCM) likewise offers an opportunity for such improvements. However, most current ODH and OCM processes produce carbon dioxide and carbon monoxide by-products at significantly higher levels than in the currently practiced steam cracking of ethane process. Therefore, there is a need for improved systems and methods that that can efficiently separate these unwanted by-products from the desired olefin products.

SUMMARY OF THE INVENTION

The inventors have discovered that carbon monoxide may be removed from the product stream produced by ODH and OCM of mixed hydrocarbon streams by oxidation with water as an oxidation agent or with a selective oxygen transfer agent (OTA) to form $CO_2$. The $CO_2$ may then be more conveniently removed from the product stream. Importantly, both of these oxidation strategies are performed at reaction conditions that do not further oxidize the product stream. This offers the benefit of minimal or no production of undesirable oxidation products such as alcohols and aldehydes, for example. According to certain embodiments, the inventive method and system offer improved process efficiency by using the same oxygen transfer agent to both effect the ODH and/or the OCM and to oxidize the CO to $CO_2$, by merely changing the reaction conditions for each step. This may be done by cycling the reaction conditions in a single reactor, or by feeding the product stream from the ODH and/or OCM step including the OTA to a subsequent reactor. Alternatively, or in addition, the water that is produced as a side product of the ODH/OCM step may be used to carry out the oxidation of the CO to $CO_2$.

The oxidation of carbon monoxide to carbon dioxide with concomitant production of hydrogen using water as the oxidant is also known as the Water Gas Shift (WGS) reaction. For the ODH process, it is important to transform the carbon oxide products to essentially all carbon dioxide so that conventional carbon dioxide removal technologies, such the Benfield process or amine extraction, may be employed to adequately remove all carbon oxides from the olefin product stream.

In one embodiment, carbon monoxide (CO) is removed by the reaction with a selective oxygen transfer agent (OTA). In this process, CO is oxidized to $CO_2$ by the stoichiometric reduction of the OTA, equation 1.

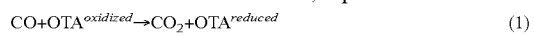

$$CO + OTA^{oxidized} \rightarrow CO_2 + OTA^{reduced} \quad (1)$$

$$OTA^{reduced} + O_2 \rightarrow OTA^{oxidized} \quad (2)$$

In a separate step, the reduced OTA may be re-oxidized (regenerated) with an oxygen containing gas, such as air.

In another embodiment, a process for the oxidative removal of CO from ODH product streams utilizes water as the oxidant. This process is similar to the well-known Water Gas Shift (WGS) process and may be performed either with, or without a catalyst.

A method of converting CO to $CO_2$ is provided. The method comprises, consists of or consists essentially of the following steps.
  a) Contacting a first process stream comprising the CO and at least one of C1 to C12 saturated and unsaturated hydrocarbons with an oxygen transfer agent.

b) Oxidizing at least a portion of the CO to $CO_2$ and reducing at least a portion of the oxygen transfer agent to a reduced oxygen transfer agent, at reaction conditions, to provide a second process stream comprising the $CO_2$, the reduced oxygen transfer agent, and the at least one of C1 to C12 saturated and unsaturated hydrocarbons. In step b), the C1 to C12 saturated and unsaturated hydrocarbons are not further oxidized.

The oxygen transfer agent comprises, consists of or consists essentially of at least one of the following:
i) water; ii) at least one reducible metal oxide; iii) at least one reducible chalcogen; mixtures of any combination of two or more of i), ii), and iii).

A system for oxidatively converting CO to $CO_2$ is also provided. The system comprises, consists of, or consists essentially of:
at least one reactor configured for:
a) contacting a first process stream comprising the CO and at least one of C1 to C12 saturated and unsaturated hydrocarbons with an oxygen transfer agent; and
b) oxidizing at least a portion of the CO to $CO_2$, at reaction conditions, and reducing at least a portion of the oxygen transfer agent to provide a second process stream comprising the $CO_2$, the reduced oxygen transfer agent, and the at least one of C1 to C12 saturated and unsaturated hydrocarbons; wherein the at least one of C1 to C12 saturated and unsaturated hydrocarbons are not further oxidized.

The oxygen transfer agent comprises, consists of or consists essentially of at least one of:
i) water; ii) at least one reducible metal oxide; iii) at least one reducible chalcogen; any combination of two or more of i), ii), and iii).

A method of converting CO to $CH_4$ is provided. The method comprises, consists of or consists essentially of:
a) contacting a first process stream comprising the CO and at least one C1 to C12 saturated and unsaturated hydrocarbons with a hydrogenation catalyst and a source of $H_2$; and
b) reacting at least a portion of the CO with the $H_2$, at reaction conditions, to provide a second process stream comprising the $CH_4$ and water.

The first process stream comprising the CO is a hydrocarbon product stream resulting from the oxidative coupling of methane or oxidative dehydrogenation of hydrocarbons.

According to another embodiment, a method of converting CO to $CH_4$ is provided.

The method comprises, consists of or consists essentially of the following steps.
a) contacting a first process stream comprising the CO and at least one C1 to C12 saturated and unsaturated hydrocarbons with a hydrogenation catalyst and a source of $H_2$; and
b) reacting at least a portion of the CO with the $H_2$, at reaction conditions, to provide a second process stream comprising the $CH_4$ and water.

The at least one of C1 to C12 unsaturated hydrocarbons are not reduced in step b); and the first process stream comprising the CO is a hydrocarbon product stream resulting from the oxidative coupling of methane or oxidative dehydrogenation of hydrocarbons.

According to an embodiment, a system for converting CO to $CH_4$ is provided. The system comprises, consists of, or consists essentially of:

at least one reactor configured for:
a) contacting a first process stream comprising the CO and at least one C1 to C12 saturated and unsaturated hydrocarbons with a hydrogenation catalyst and a source of $H_2$; and
b) reacting at least a portion of the CO with the $H_2$, at reaction conditions, to provide a second process stream comprising the $CH_4$ and water.

The at least one of C1 to C12 unsaturated hydrocarbons are not reduced in step b); and the first process stream comprising the CO is a hydrocarbon product stream resulting from the oxidative coupling of methane or oxidative dehydrogenation of hydrocarbons.

DETAILED DESCRIPTION OF CERTAIN EMBODIMENTS

Figure 1:
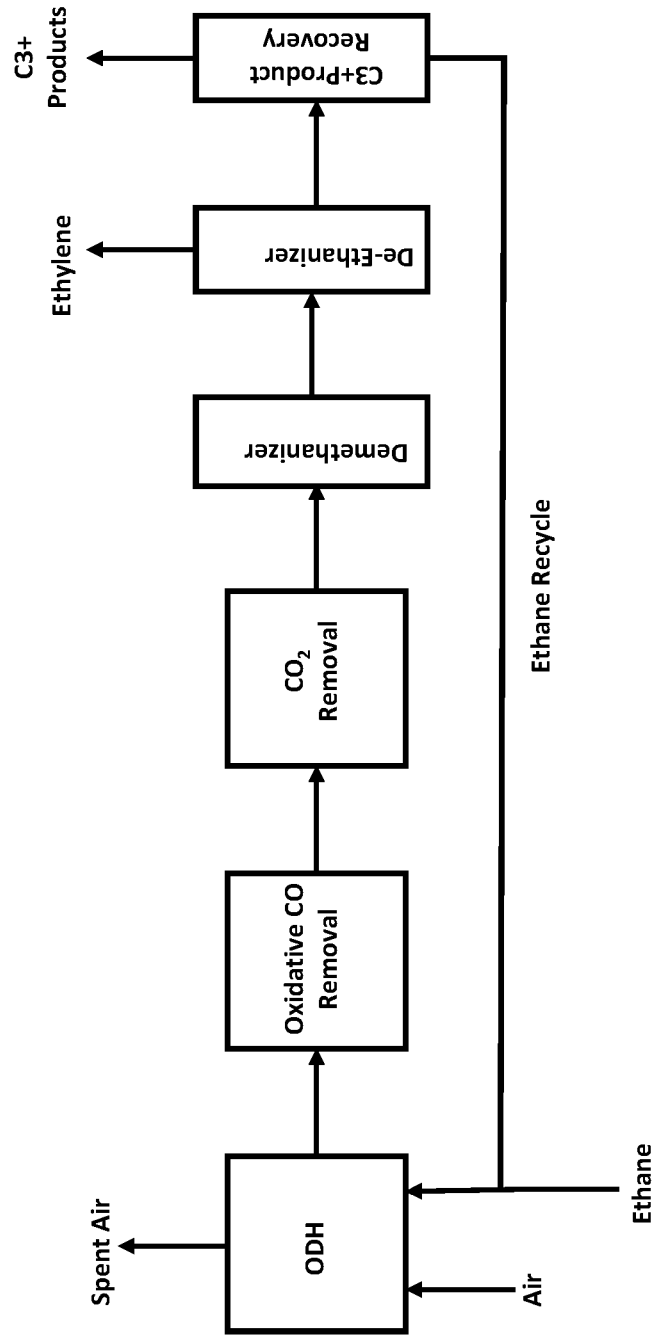
FIG. 1 shows an exemplary system according to an embodiment of the invention whereby CO is oxidized to $CO_2$ before employing techniques to remove $CO_2$.

The oxidative couple of methane (OCM) and the oxidative dehydrogenation (ODH) of ethane and propane to olefins offer production routes that can significantly reduce $CO_2$ emissions and virtually eliminate NOx emissions from world scale plants. ODH is a selective process that produces primarily ethylene and water as products, and is an exothermic reaction, shown below as reaction 1.

$$CH_3CH_3 + \tfrac{1}{2}O_2 \rightarrow CH_2CH_2 + H_2O \quad \Delta H° = -105 \text{ kJ/mol} \qquad (1)$$

The oxidative coupling of methane (OCM) reaction to produce water is likewise exothermic, shown below as reaction 2.

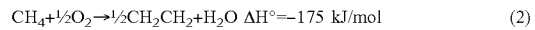
$$CH_4 + \tfrac{1}{2}O_2 \rightarrow \tfrac{1}{2}CH_2CH_2 + H_2O \quad \Delta H° = -175 \text{ kJ/mol} \qquad (2)$$

The per-pass yields of the ODH reaction and the OCM reaction are not limited by thermodynamic equilibrium, as it is in pyrolysis. The pyrolysis of ethane is shown below as reaction 3.

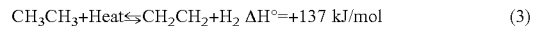
$$CH_3CH_3 + \text{Heat} \leftrightarrows CH_2CH_2 + H_2 \quad \Delta H° = +137 \text{ kJ/mol} \qquad (3)$$

The oxidative coupling of methane (OCM) and the ODH of ethane and higher hydrocarbons such a propane are therefore reactions of significant commercial value. The oxidative dehydrogenation of propane, likewise is an exothermic reaction and therefore is best performed in fluid bed reactors.

These conversions, either ODH of ethane or higher hydrocarbons or OCM may be done either catalytically by feeding a hydrocarbon and an oxygen containing gas, or in a redox oxygen transfer mode whereby an Oxygen Transfer Agent (OTA) supplies the necessary oxygen for the formation of water and the reaction proceeds without oxygen. Either system is exemplified by equation (4):

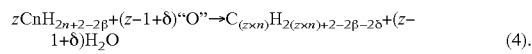

$$zC_nH_{2n+2-2\beta}+(z-1+\delta)\text{"O"}\rightarrow C_{(z\times n)}H_{2(z\times n)+2-2\beta-2\delta}+(z-1+\delta)H_2O \quad (4).$$

where z=the number of reacting molecules; n=the number of atomic units in the reacting molecule; β=the degree of unsaturation where the value is zero for single bonds, one for double bonds and molecular rings, and two for triple bonds; and δ=the change in the degree of unsaturation. The oxygen, "O" in (4) may be supplied by the reduction of a metal oxide or via the catalytic use of molecular oxygen. The present inventors have found that a single OTA may be used to effect any of the reactions exemplified by reaction (4), but that differing reaction conditions are needed for each hydrocarbon (methane, ethane, propane butanes, etc.) in the feed. Either reaction (OCM or ODH) is exemplified by equation (4), and will be referred to herein as either OCM or ODH; i.e. for the purposes of this disclosure, the terms, "oxidative coupling of methane" (OCM) and "oxidative dehydrogenation" (ODH) are considered to be interchangeable.

One of the beneficial aspects of OCM and ODH as replacement technologies for conventional steam cracking is that the relative yields to the important olefin and aromatic products are very similar. Therefore, similar product recovery technologies may be employed for the removal and sale of the products. The major difference in the oxidative production of olefins compared to their production via steam cracking is in the formation of higher levels of carbon oxide byproducts. Typical yield comparisons between ethane steam pyrolysis and ethane ODH are shown in Table 1.

TABLE 1

Comparison of steam cracking and ODH yield, wt %

|  | Steam Cracking* | ODH** |
| --- | --- | --- |
| Ethane | 23.35% | 6.02% |
| Methane | 2.35% | 4.68% |
| Acetylene | 0.31% | 0.10% |
| Ethylene | 34.88% | 40.97% |
| Propylene | 0.75% | 2.93% |
| Propane | 0.08% | 0.31% |
| Butadiene | 1.20% | 1.70% |
| Butenes | 0.13% | 1.77% |
| Butanes | 0.14% | 0.06% |
| C5's | 0.00% | 0.61% |
| Benzene | 0.31% | 3.26% |
| Toluene | 0.05% | 0.11% |
| CO | 0.03% | 2.34% |
| $CO_2$ | 0.01% | 3.68% |
| Coke | 0.39% | 0.00% |
| Hydrogen | 2.70% | 0.85% |
| Water | 33.33% | 30.61% |
| Total | 100.00% | 100.00% |

*From H. Zimmermann and R. Walzl, Linde, "Ullman's Encyclopedia of Industrial Chemistry", Wiley, 2012, p. 477.
**From U.S. Pat. Nos. 10,138,182 B2; 10,968,149 B2; and 10,919,027 B1, all of which are incorporated by reference herein in their entireties for all purposes.

Figure 2:
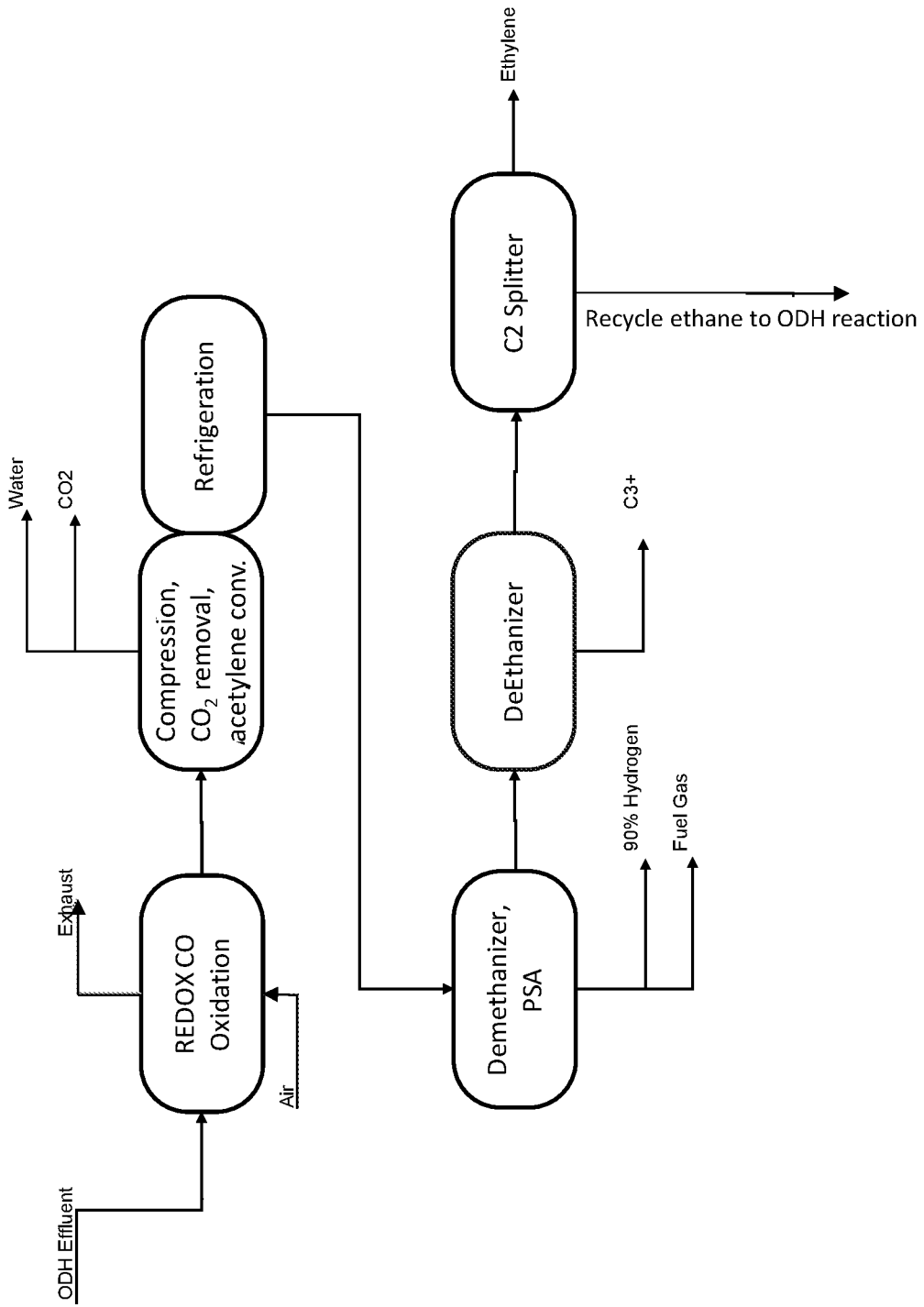
FIG. 2 shows an embodiment of an exemplary system according to an embodiment of the invention whereby the byproduct CO is oxidized by an OTA and removed as $CO_2$ according to the invention.
Figure 4:
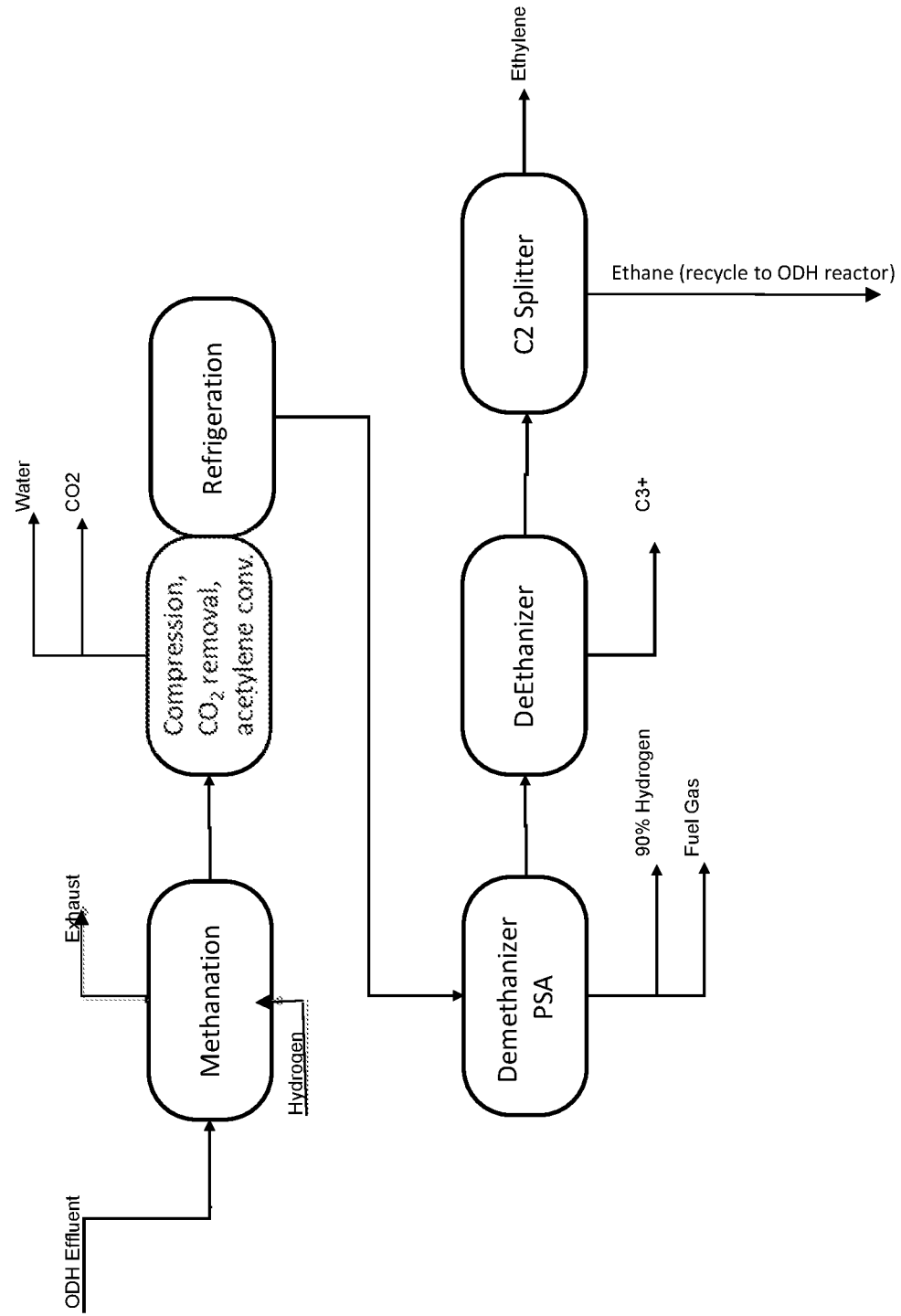
FIG. 4 shows another exemplary system according to an embodiment of the invention whereby CO is hydrogenated to methane for separation.

As shown in Table 1, ODH gives higher yields of ethylene, and other valuable olefin and aromatic products compared to steam cracking. However, the less desirable products of carbon dioxide and carbon monoxide are also higher for ODH. As shown in FIG. 1, carbon dioxide and carbon monoxide should be removed before the cryogenic removal of methane and further purification of the olefins. Typical processes for the removal of carbon dioxide from hydrocarbon streams, such as the Benfield process or amine extraction, are suitable for $CO_2$ removal but will not function to remove the levels of carbon monoxide in the ranges produced by the typical ODH processes. As shown in FIG. 4, in an embodiment, methanation of the carbon monoxide may also be used to reduce the CO level. As shown in FIG. 2, the methanation of CO to $CH_4$ uses hydrogen.

Methods for Oxidative Conversion of Carbon Monoxide in a Mixed Hydrocarbon Product Stream to a Product Stream with the Selective Conversion of Carbon Dioxide to Carbon Monoxide FIG. 1 shows an embodiment of the methods and systems for converting CO to $CO_2$ according to certain aspects of the invention. As shown in the figure, ethane and air are fed to an ODH reactor. The feed to the ODH reactor may also include other saturated hydrocarbons, such as methane and/or at least one of C3 to C12 hydrocarbons. The air provides oxygen. As discussed below, the oxygen is optional. In the ODH reactor, the hydrocarbons are oxidatively dehydrogenated at oxidative dehydrogenation reaction conditions to produce a process stream that includes saturated and unsaturated hydrocarbons, water and a reduced oxygen transfer agent, as well as CO. The CO may be oxidatively converted to $CO_2$ using an oxygen transfer agent as described herein. According to certain embodiments, described in more detail below, at least a portion of the CO is oxidized to $CO_2$ and at least a portion of the oxygen transfer agent is reduced to a reduced oxygen transfer agent, at reaction conditions, to provide the second process stream comprising the $CO_2$, the reduced oxygen transfer agent, and the at least one of C1 to C12 saturated and unsaturated hydrocarbons which emerge from the CO oxidation step as shown in FIG. 1. Importantly, the C1 to C12 saturated and unsaturated hydrocarbons are not further oxidized in the CO oxidation step. The oxygen transfer agent comprises at least one of: i) water; ii) at least one reducible metal oxide; iii) at least one reducible chalcogen; or mixtures of any combination of two or more of i), ii), and iii). The resulting $CO_2$ may be removed according to methods as are known in the art. The process stream emerging from the $CO_2$ removal step may be subjected to a step of demethanization. According to some embodiments of the invention, the demethanizer may be place prior to the step where the CO is converted to $CO_2$. The demethanization may done by pressure swing absorption, flashing, or distillation, for example. Ethylene as a product is then taken off. Finally, the C3 and higher products are taken off and the remaining ethane (and/or other mixed hydrocarbons) is recycled back to the ODH reactor.

FIG. 2 shows another embodiment of the invention. In FIG. 2, the stream labeled ODH effluent is the product of oxidative coupling of methane or oxidative dehydrogenation of hydrocarbons at hydrocarbon oxidation reaction conditions to produce a process stream that includes at least one of CO and C1 to C12 saturated and unsaturated hydrocarbons. This stream is then sent to the REDOX CO oxidation reactor. In this reactor, the CO is oxidized to $CO_2$, using an oxygen transfer agent. The oxygen transfer agent is therefore reduced. Importantly, the reaction conditions in this reactor are such that the C1 to C12 saturated and unsaturated hydrocarbons are not further oxidized to undesirable acids, alcohols, or aldehydes. According to various embodiments of the invention, the oxygen transfer agent may be the same as that used to oxidatively produce the ODH effluent that is fed to the CO oxidation step. The REDOX CO oxidation reactor produces a stream that now is enriched in $CO_2$ and is sent to be further processed to remove $CO_2$ and water. The effluent from this operation may be refrigerated and sent to the demethanizer, which may be, for example, a pressure swing absorber unit. According to some embodiments of the invention, the demethanizer may be placed prior to the step where the CO is converted to $CO_2$. Hydrogen and fuel gas are taken off from the demethanizer and the remaining stream is sent to the de-ethanizer, where the C3 and higher hydrocarbons are taken off and sent to the C2 splitter where the desired ethylene product is taken off. The remaining ethane and other mixed hydrocarbons are recycled to the ODH reactor.

Figure 3:
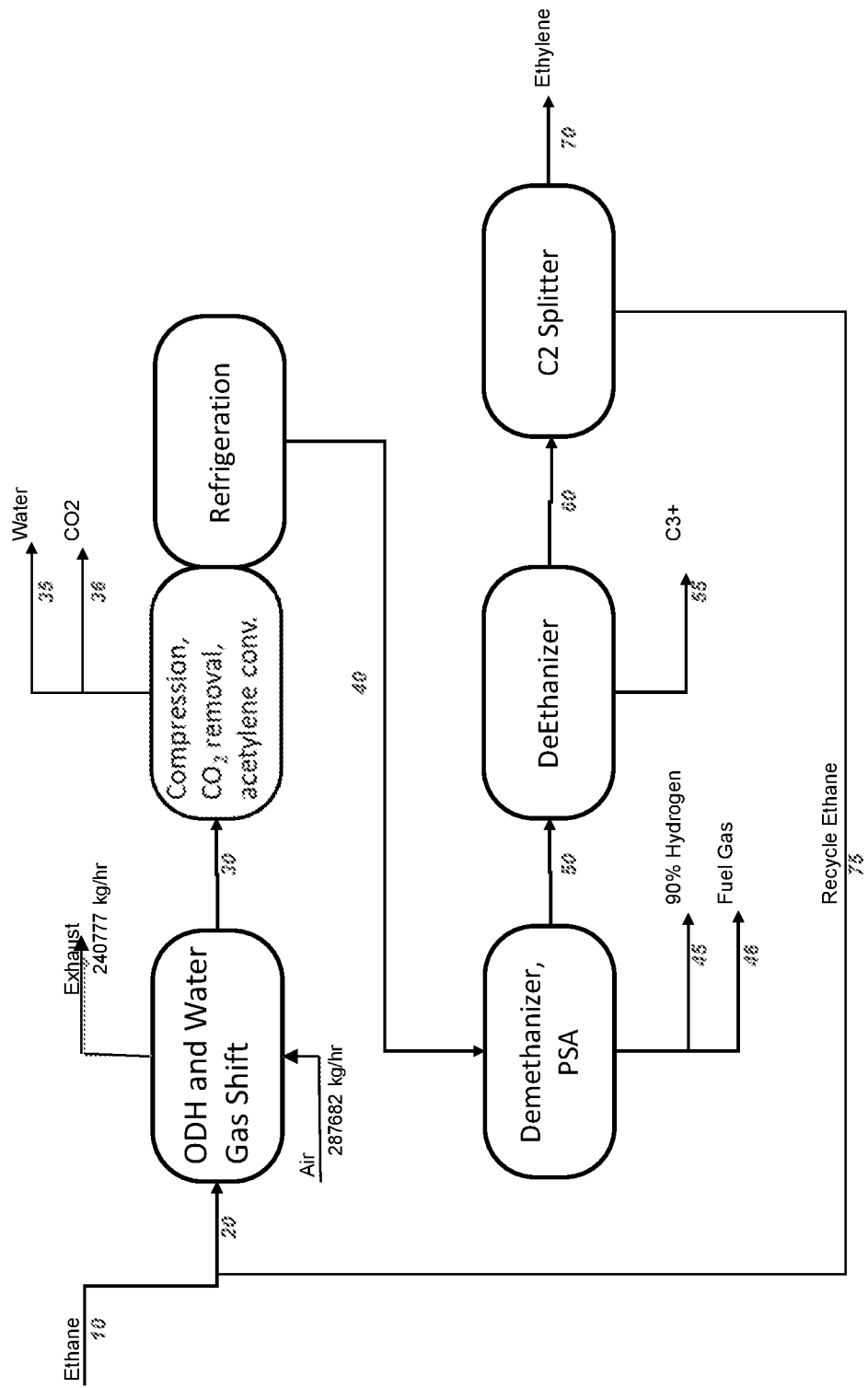
FIG. 3 shows an embodiment of an exemplary system according to an embodiment of the invention whereby the byproduct CO is oxidized by water via the WGS reaction and removed as $CO_2$ according to the invention.

FIG. 3 shows an embodiment of the invention where water is used as the oxidant to convert the CO in the ODH effluent stream to $CO_2$, in an analogous reaction to the water gas shift reaction. As shown in FIG. 3, ethane is depicted as a model compound in the feed stream 10 that is fed to the ODH and water gas reactor. It should be understood that the stream 10 could also include other hydrocarbons. As shown in FIG. 3, the ODH and water gas shift are shown as a single reactor. However, according to another embodiment, two reactors could also be used, such that the ODH is carried out in a first reactor and then the effluent from that ODH reactor, comprising mixed saturated and unsaturated hydrocarbons, would then be fed to a water gas shift reactor. As discussed above, the conditions in the ODH/water gas shift reactor are such that the hydrocarbons are not further oxidised to form undesirable alcohols, acids or aldehydes. Stream 30, which is now enriched in $CO_2$ and also contains the products of the ODH reaction is fed to a downstream system to remove the $CO_2$ and to purify the desired ethylene product. The removal of the $CO_2$ and the purification of ethylene may be done according to methods as are known and used in the art. For example, the demethanizer could be placed prior to the $CO_2$ removal. As shown in FIG. 3, in the compression, $CO_2$ removal and acetylene conversion step produces streams 35 (water) and 36 ($CO_2$). The product of the compression, $CO_2$ removal and acetylene conversion step (sans water and $CO_2$) is refrigerated and that cold stream 40 is passed to the demethanizer. In the example shown in FIG. 3, the demethanization is done via pressure swing absorption. The demethanized stream 50 is passed to the de-ethanizer, where the C3 and higher hydrocarbons are removed as stream 55. This may be done via a distillation process, for example. Stream 55 may be a product stream used as fuel or could be recycled back to the ODH reactor. Stream 60, which includes ethane and ethylene is sent to the C2 splitter where the product ethylene stream 70 is produced. The separated the ethane from the C2 splitter 75 is recycled back to the ODH reaction.

FIG. 4 shows another embodiment of the invention. In this embodiment, the CO in the product stream from the ODH reactor (ODH Effluent) is converted to methane by reaction with hydrogen in a methanation process, rather than being oxidized to $CO_2$ as shown in FIG. 2. Importantly, the reaction conditions in the methanation reactor are selected such that the unsaturated hydrocarbons in the feed are not hydrogenated. According to various embodiments, a hydrogenation catalyst is generally used to carry out the methanation. Methanation can be conducted in multiple stages. The first stage may use an iron oxide with chromium catalyst at high temperature (300-560° C.) which gets CO concentrations down to 2-3%. The second stage may use Cu/Zn oxide with alumina, at 200-260° C. Although a single reactor is shown in FIG. 3, two or more reactors may be employed if needed. The adiabatic temperature rise for methanation of this stream may be quite high-about 450° C. for this case. This is because of the relatively high CO concentration and the fact that hydrogen, which makes up over half of the feed on a molar basis, has a low heat capacity. Therefore, the reactor may be a packed shell-and-tube type vertical reactor, generating high pressure steam on the shell side.

A method to convert CO to $CO_2$ is provided. The method comprises:
a) contacting a first process stream comprising the CO and at least one of C1 to C12 saturated and unsaturated hydrocarbons with an oxygen transfer agent; and
b) oxidizing at least a portion of the CO to $CO_2$ and reducing at least a portion of the oxygen transfer agent to a reduced oxygen transfer agent, at reaction conditions, to provide a second process stream comprising the $CO_2$, the reduced oxygen transfer agent, and the at least one of C1 to C12 saturated and unsaturated hydrocarbons; such that the C1 to C12 saturated and unsaturated hydrocarbons are not further oxidized. The oxygen transfer agent for the oxidation of the CO to the $CO_2$ comprises at least one of: i) water; ii) at least one reducible metal oxide; iii) at least one reducible chalcogen; mixtures of any combination of two or more of i), ii), and iii).

According to an embodiment of the invention, the method may further include, prior to step a), a step a1). Step a1) is oxidative coupling of methane or oxidative dehydrogenation of hydrocarbons at hydrocarbon oxidation reaction conditions to produce the first process stream. The hydrocarbon reaction conditions are understood to be different from the reaction conditions to carry out the oxidation of the CO to the $CO_2$. Step a1) is oxidative coupling of methane or oxidative dehydrogenation of hydrocarbons at hydrocarbon oxidation reaction conditions. For example, the step a1) takes place at higher temperatures than step a). The step a1) oxidative coupling of methane or oxidative dehydrogenation of hydrocarbons takes place at temperatures of 750° C. to 850° C. or even higher. The step a) oxidation of CO to $CO_2$ is done at considerably lower temperatures, for example, from 350° C. to 450° C., or from 250° C. to 500° C., or from 200° C. to 400° C., or from 350° C. to 500° C.

According to another embodiment of the invention, the oxygen transfer agent that is used to carry out the conversion of CO to $CO_2$ may be i) water and the step a1) oxidative coupling of methane or oxidative dehydrogenation of hydrocarbons produces the water that is used as the oxygen transfer agent in step a). According to an embodiment of the invention, step a1) and step a) may be performed in the same reactor. In this case, the water produced as a side product is therefore used to carry out the oxidation of the CO to the $CO_2$. Appropriate catalysts may be used for this oxidation of the CO to $CO_2$ using water as the oxidant, according to some embodiments.

According to another embodiment, the oxygen transfer agent used to convert the CO to $CO_2$ may be at least one of ii) at least one reducible metal oxide or iii) at least one reducible chalcogen and the same oxygen transfer agent ii) or iii) may be used in step a1) and step a). According to this embodiment, the reaction conditions during the CO to $CO_2$ conversion step a) are different from the reaction conditions during the ODH reaction of step a1). It is important that the conditions of step a) do not further oxidize the mixed at least one of C1 to C12 saturated and unsaturated hydrocarbons. According to an embodiment of the invention, step a1) and step a) may be performed in the same reactor. This is done by changing reaction conditions such that the hydrocarbon feed stream reactor is first oxidatively dehydrogenated as step a1), and then adjusting the reaction conditions such that the CO produced in step a1) is converted to $CO_2$ in step a), without further oxidizing the hydrocarbons in the reactor.

According to an embodiment, the step a) takes place in the presence of less than 5 wt % of $O_2$ with respect to the total amount of CO in the first process stream. According to some embodiments the amount of oxygen in the first process stream is at most 5 wt %, or at most 4.8, 4.6, 4.4, 4.2, 4, 3.8, 3.6, 3.4, 3.2, 3, 2.8, 2.6, 2.4, 2.2, 2, 1.8, 1.6, 1.4, 1.2, 1, 0.9, 0.8, 0.7, 0.6, 0.5, 0.4, 0.3, 0.2, or at most 0.1 wt % of $O_2$ with respect to the total amount of CO in the first process stream. According to some embodiments there is at most 950 ppm wt, or at most 900, 850, 800, 750, 700, 650, 600, 550, 500, 450, 400, 350, 300, 250, 200, 150, 100, 90, 80, 70, 60, 50, 40, 30, 20, 10, 5, 1, 0.5, or 0.1 ppm wt $O_2$ with respect to the total amount of CO in the first process stream. According to an embodiment, there is no $O_2$ in the first process stream.

According to an embodiment, the oxygen transfer agent is the reducible metal oxide ii) and/or the reducible chalcogen iii) and the method further comprises a step c) contacting the reduced oxygen transfer agent with a third process stream comprising molecular oxygen to provide a regenerated oxygen transfer agent.

According to an embodiment, the method further comprises a step d) feeding the regenerated oxygen transfer agent to step a) as the oxygen transfer agent.

According to another embodiment, the method further comprises a step d) feeding the regenerated oxygen transfer agent to step a) converting the CO to $CO_2$ and/or to step a1) the ODH reaction as the oxygen transfer agent.

According to an embodiment, the method further comprises a step e) removing at least a portion of the $CO_2$ from the second process stream. This removal may be done according to methods as are known in the art, such as amine extraction, membrane separation, cryogenic separation and the like.

According to another embodiment of the method of converting the CO to $CO_2$, the oxygen transfer agent is i) water and the reduced oxygen transfer agent comprises $H_2$. This method may optionally be performed in the presence of suitable catalysts, such as those based on Mn, Fe, Cu, Zn, Ce, Cr, Co, Ni, oxides thereof; rare earth oxides; and/or combinations of any of the forgoing, for example.

Method of Converting CO to $CH_4$:

According to another embodiment of the invention, the CO is removed by converting it to methane, $CH_4$. A method of converting CO to $CH_4$ is provided. The method comprises, consists of, or consists essentially of:
 a) contacting a first process stream comprising the CO and at least one C1 to C12 saturated and unsaturated hydrocarbons with a hydrogenation catalyst and a source of $H_2$; and
 b) reacting at least a portion of the CO with the $H_2$, at reaction conditions, to provide a second process stream comprising the CH Step a1) is oxidative coupling of methane or oxidative dehydrogenation of hydrocarbons at hydrocarbon oxidation reaction conditions and water. Importantly in this method, the at least one of C1 to C12 unsaturated hydrocarbons in the first process stream are not reduced in step b). The first process stream comprising the CO is a hydrocarbon product stream resulting from the oxidative coupling of methane or oxidative dehydrogenation of hydrocarbons. Therefore, it is clearly desirable for the valuable unsaturated products in the first process stream to not be reduced back to saturated hydrocarbons. Accordingly, the reaction conditions, such as suitable gas hourly space velocities, pressures and temperatures are selected so as to avoid this. Suitable catalysts may be used to hydrogenate the CO to methane. Non-limiting examples are $Pd/Al_2O_3$, Cr, Zn, etc. According to an exemplary embodiment, the CO to methane process may be carried out in two stages: over a chromium catalyst at high temperature (300-560° C.) which gets CO concentrations down to 2-3%. The second stage may use Cu/Zn oxide with alumina, at 200-260° C.

Systems for Oxidatively Converting CO to $CO_2$:

A system for oxidatively converting CO to $CO_2$ is provided. The system comprises, consists of, or consists essentially of:
 at least one reactor configured for:
 a) contacting a first process stream comprising the CO and at least one of C1 to C12 saturated and unsaturated hydrocarbons with an oxygen transfer agent; and
 b) oxidizing at least a portion of the CO to $CO_2$, at reaction conditions, and reducing at least a portion of the oxygen transfer agent to provide a second process stream comprising the $CO_2$, the reduced oxygen transfer agent, and the at least one of C1 to C12 saturated and unsaturated hydrocarbons; wherein the at least one of C1 to C12 saturated and unsaturated hydrocarbons are not further oxidized. The oxygen transfer agent comprises, comprises, consists of or consists essentially of at least one of:
 i) water; ii) at least one reducible metal oxide; iii) at least one reducible chalcogen; or any combination of two or more of i), ii), and iii).

According to an embodiment, the first process stream is produced by a step a1) comprising, consisting of, or consisting essentially of oxidative coupling of methane or oxidative dehydrogenation of hydrocarbons at hydrocarbon oxidation reaction conditions.

According to an embodiment, the oxygen transfer agent is i) water and the step a1) produces water that is used as the oxygen transfer agent in step a). According to an embodiment of the system, step a1) and step a) are performed sequentially in the same reactor. According to an embodiment, the oxygen transfer agent is ii) or iii) and the step a1) utilizes the same oxygen transfer agent ii) as step a).

According to an embodiment of the system, the oxygen transfer agent comprises, consists of, or consists essentially of ii), iii) or a combination thereof and the at least one reactor comprises an inlet and an outlet. The system further comprises, consists of, or consists essentially of a regeneration unit in communication with the inlet and the outlet, wherein the regeneration unit is constructed and arranged to:
 c) receive at least a portion of the reduced oxygen transfer agent from the outlet;
 d) contact the at least a portion of the reduced oxygen transfer agent with a gas comprising molecular oxygen to produce a regenerated oxygen transfer agent; and
 e) feed the regenerated oxygen transfer agent to the inlet.

According to an embodiment, the system further comprises, consists of, or consists essentially of a purification unit in communication with the at least one reactor, wherein the purification unit is constructed and arranged to remove at least a portion of the $CO_2$ from the second process stream. This purification unit may be an amine or other base absorber, a cryogenic distillation unit, a caustic wash, or a membrane separation unit, for example.

Systems for Converting CO to $CH_4$:

A system for converting CO to $CH_4$ is provided. The system comprises, consists of or consists essentially of:
 at least one reactor configured for:
 a) contacting a first process stream comprising, consisting of, or consisting essentially of the CO and at least one C1 to C12 saturated and unsaturated hydrocarbons with a hydrogenation catalyst and a source of $H_2$; and b) reacting at least a portion of the CO with the $H_2$, at reaction conditions, to provide a second process stream comprising, consisting of, or consisting essentially of the $CH_4$ and water;

wherein the at least one of C1 to C12 unsaturated hydrocarbons are not reduced in step b); and wherein the first process stream comprising the CO is a hydrocarbon product stream resulting from the oxidative coupling of methane or oxidative dehydrogenation of hydrocarbons.

Reactors:

The reactors employed in certain embodiments of the system or method directed to the use of an oxygen transfer agent (OTA) for the in-stream oxidation of CO to $CO_2$ as described herein could be any system known to transport a solid particle between a reactor and a regenerator zone. Such transport systems are generally known to one of ordinary skill in the art. While not intending to be limited by these examples, useful reactors are circulating fluid beds such as fluid catalyzed cracking units, fluidized bed reactors, moving bed reactors, either co-current or counter current flow and bubbling bed reactors with means of transport of solids between the beds, or any circulating system as known in the art. The reactors could also be fixed, or non-circulating fluid bed, reactors whereby reaction gases are switched at appropriate times between oxidation conditions and re-oxidation conditions.

Regeneration Units:

Suitable regeneration units utilized in the system or method disclosed in the first embodiment herein to re-oxidize the reduced oxygen transfer agent may be any of those types as known and used in the art to regenerate solid particulates, especially, but not limited to those that are suitable for contacting a particulate solid with a gas. For example, fluidized beds, rotating moving beds, recirculating fluidized beds, moving beds, either co-current or counter current flow and bubbling beds with means of transport of solids between the beds, or any circulating system as known in the art may be used to regenerate the oxygen transfer agent. The regeneration reactors could also be fixed, or non-circulating fluid bed, reactors whereby reaction gases are switched at appropriate times between oxidation conditions and re-oxidation conditions.

Reaction Conditions for the Oxidative Conversion of CO to $CO_2$:

According to some embodiments of the system and method, one or more of the reactor conditions to carry out the oxidative conversion of CO to $CO_2$ with a selective OTA in the presence of the hydrocarbon product from OCM or ODH.

According to some embodiments, the reaction conditions for the use of OTA to convert CO to $CO_2$ may include the presence of essentially no molecular oxygen during the oxidative conversion of CO. In this embodiment, at least a portion of the oxygen transfer agent may be reduced to produce a reduced oxygen transfer agent. Without wishing to be bound by theory, this condition means that the oxygen needed for the oxidative conversion of CO may be supplied by the at least one oxygen transfer agent.

According to other embodiments, molecular oxygen may be present during the oxidative conversion of CO to $CO_2$. In particular, less than 5 wt %, less than 4 wt %, less than 3 wt %, less than 2 wt %, less than 1 wt %, less than 0.5 wt %, less than 1000 ppm weight, less than 500 ppm weight of molecular oxygen with respect to the total amount of CO in the first process stream, the oxygen transfer agent and the molecular oxygen is present during the CO oxidative conversion step. Less than 1000 ppm weight of molecular oxygen is preferred. Non-limiting examples of sources of molecular oxygen are air, or molecular oxygen-containing streams resulting from other chemical processes.

According to some embodiments the oxidative reaction conditions in step b) may include temperatures of from 325-650° C. and gas hourly space velocities of 1,000 to 10,000 $hr^{-1}$. Other suitable temperatures may be from 300° C. to 1000° C., 350° C. to 1000° C., 400° C. to 1000° C., 400° C. to 800° C., or from 500° C. to 700° C. Pressure may be from sub-atmospheric to super-atmospheric with a range of 0.1 to 100 atm. In other embodiments, the pressure range may be 0.9 to 10 atm. Other pressure ranges may be from 0.9 to 1.5, 0.5 to 2, 0.9 to 5, 0.9 to 7, or 0.9 to 1.1 atm. According to some embodiment, the temperature may be from 600-950° C., or from 500-900° C. or from 700-900° C. or from 800-850° C. For example the temperature may be at least 250° C., or at least 300, 325, 350, 400, 400, 450, 500, 550, 600, 650, 700, or at least 750° C. For example, the temperature may be at most 1000° C., or at most 950, 900, 850, 800, 750, 700, or at most 650° C.

While in some cases it might be desirable to separate the feed components before introduction to the reactor vessel, it may also be beneficial not to separate some of the hydrocarbons and allow the reactor conditions to effect separation. In this instance of the present inventive system or method, as an example, methane and ethane could be fed to one reactor zone where ethane primarily reacts at one set of reactor conditions to form olefin products and then separation occurs between the unreacted methane and olefins formed from ODH.

In another embodiment of the present system or method, multiple reactors may be used to selectively feed hydrocarbons for oxidative dehydrogenation under appropriate conditions to form olefins and other reactors under different conditions to oxidatively convert CO to $CO_2$. According to certain embodiments of the system or method, the feature of multiple reactors utilizing a single regeneration unit can allow for a single OTA to be used for both hydrocarbon ODH or OCM and other reactors to be used for CO oxidation, the multiple reactors allowing for optimization of reaction conditions for each conversion.

In another embodiment of the present system and method, CO is converted to $CO_2$ and hydrogen in the presence of steam similar to the well-known Water Gas Shift (WGS) process and may be performed either with, or without a catalyst. In this embodiment, the oxidation transfer agent is water, and it is reduced to $H_2$. While not to be limited by theory, the materials and catalysts for this process of converting CO to $CO_2$ could be any materials typically used for WGS such as catalysts comprising, iron, zinc, nickel, rhodium, iridium, platinum, palladium, gold, ruthenium, or other metals useful for the WGS reaction. A key aspect for the use of WGS for CO removal is that it operates above 300° C. and importantly does not also co-produce oxygenated products such as alcohols or acetic acid, or aldehydes during the WGS separation process. Oxygenated products such as these, if formed during the CO removal process may add greatly to the cost for recovery of polymer grade olefins. In addition, low alcohol content in polymer grade ethylene is generally required in order not to be a poison for typical polymerization catalysts.

Reactions:

The systems disclosed in the present invention may be used for the removal of CO by-products from the oxidative dehydrogenation of hydrocarbon feeds that may proceed according to the reaction:

$$zCnH_{2n+2-2\beta}+(z-1+\delta)\text{"O"} \rightarrow C_{(z \times n)}H_{2(z \times n)+2-2\beta-2\delta}+(z-1+\delta)H_2O$$

wherein: z=the number of reactant molecules; n=the number of atomic units in the reactant molecule; β=the degree of unsaturation in the reactant molecule, where the value is zero for single bonds, and one for double bonds and molecular rings; δ=the change in the degree of unsaturation from the reactant molecule to the product molecule; and "O" is atomic oxygen; and wherein the atomic oxygen is supplied by the at least one oxygen transfer agent. According to some embodiments, z=2, n=1, β=0, and δ=0. In particular this means that the reaction may include the oxidative coupling of methane to form ethylene. According to other embodiments, z=1, n=2, β=0, and δ=1. In particular, this means that the reaction may include the oxidative dehydrogenation of ethane to form ethylene. The oxidative dehydrogenation may include more than one reaction. Non-limiting examples of such multiple reactions may include: skeletal isomerization of olefins; oxidative dehydrogenation of methane to ethane and ethylene, and oxidative dehydrogenation of ethane to ethylene and higher olefins such as propylene and butylene.

CO and $CO_2$ are generally also produced in the oxidative dehydrogenation systems and must be efficiently removed. In one embodiment of the present disclosure, CO is oxidized to $CO_2$ using an OTA/redox cycle as in equations 1 and 2. In another embodiment, the oxidation of CO may use molecular oxygen $$CO+\tfrac{1}{2}O_2 \rightarrow CO_2$$

In yet another embodiment, CO is reacted with steam and converted to $CO_2$ and hydrogen with or without a catalyst.

$$CO+H_2 \rightleftharpoons CO_2+H_2$$

Hydrocarbon Feed:

Suitable mixed hydrocarbon feeds for use in embodiments of the present system or method invention may be selected from methane; ethane; propane; isomers of butane; isomers of butene, isomers of pentane; isomers of pentene; isomers of hexane; cyclohexane; isomers of hexene; cyclohexene; naphtha; gas oil; and mixtures thereof. As used here, the term "mixed hydrocarbon feed" means a feed including two or more different hydrocarbons, for example a feed stream containing methane and ethane.

Oxygen Transfer Agents:

Non-limiting examples of suitable oxygen transfer agents for use in embodiments of the present invention may include at least one element selected from the group consisting of, Mn, Fe, Mo, Ti, V, Pr, Cu, La, Ga and mixtures thereof. A suitable oxygen transfer agent may include Li/Mn/B/MgO, Li/Mn/B/CaSO₄/MgO, Na/Pr₆O₁₁, and mixtures thereof. In an embodiment, the oxygen transfer agent may further include at least one promotor selected from the group consisting of, alkaline metals, alkaline earth metals, boron, sulfur, salts of tungstic acid, salts of halides, and mixtures thereof. Other suitable oxygen transfer agents that may be used in embodiments of this invention are those that are described in U.S. patent application Ser. No. 16/800,883 filed on Feb. 25, 2020; U.S. Ser. No. 16/845,815 filed on Apr. 10, 2020; and U.S. Ser. No. 16/877,992 filed May 20, 2020, the contents of each of which are incorporated by reference herein in their entireties for all purposes.

For example, the oxygen transfer agent for converting CO to $CO_2$ may be at least one reducible metal oxide that comprises, consists of, or consists essentially of at least one of alkaline earth metals, actinide metals, lanthanide metals trivalent transition metals, or combinations thereof. The at least one reducible metal oxide may comprise, consist of, or consist essentially of at least one of Li/Mn/B/MgO, Li/Mn/B/CaSO₄/MgO, Na/Pr₆O₁₁, Mn, Fe, Mo, Ti, V, Pr, Cu, La, Ga, Tb, Nd, Dy, or mixtures or combinations thereof. Suitable such materials are described in U.S. Pat. No. 11,046,892, the contents of which is incorporated by reference herein in its entirety for all purposes.

According to certain embodiments, any of the reducible metal oxides ii) or reducible chalcogens iii) used to convert CO to $CO_2$ as described herein may be in combination with at least one zeolite, such that inner channels of the at least one zeolite are from 3 to 8 Angstroms in size. The zeolite may be acidic in nature and the acid nature may be confined to the exterior surfaces of the zeolite. If present, the zeolite may comprise, consist of, or consist essentially of zeolite Y, ZSM-5. The reducible metal oxides ii) or reducible chalcogens iii) may comprise, consist of, or consist essentially of oxides of Mn, oxides of Cu, and/or oxides of Ca. According to certain embodiments the oxygen transfer agent ii) or iii) that is used to convert the CO to $CO_2$ may comprise, consist of, or consist essentially of at least one oxide of sulfur selected from sulfur dioxide; sulfur trioxide; $CaSO_4$; sulfate salts of Mn, Fe, Sm, Ga, Ti, W, Mo, V, Nb, Cr, K, Cs, Rb, P, Cu, Pb, Ni, As; or mixtures thereof. According to an embodiment, the at least one oxygen transfer agent ii) or iii) used to convert the CO to $CO_2$ may be selected from $MnO_2$, CuO, or CaO. According to an embodiment, the reducible metal oxide ii) may include at least one oxide of sulfur selected from sulfur dioxide; sulfur trioxide; $CaSO_4$; sulfate salts of Mn, Fe, Sm, Ga, Ti, W, Mo, V, Nb, Cr, K, Cs, Rb, P, Cu, Pb, Ni, and As; and mixtures thereof. According to an embodiment, the at least one oxygen transfer agent ii) or iii) used to convert the CO to $CO_2$ may be selected from $MnO_2$, CuO, or CaO. According to an embodiment, the reducible metal oxide ii) may be selected from oxides of La, oxides of Pr, oxides of Tb, oxides of Nd, oxides of Dy, or mixtures thereof.

According to another embodiment, the oxygen transfer agent ii) for converting CO to $CO_2$ may comprise, comprises, consist of, or consist essentially of at least one reducible metal oxide ii) that comprises, consists of, or consists essentially of at least one of $M_3BO_5$, a compound that satisfies the formula $M'_2M''BO_5$, or mixtures thereof. M is selected from alkaline earth metals, actinide metals, lanthanide metals, trivalent transition metals, and combinations thereof; M' is selected from alkaline earth metals, actinide metals, lanthanide metals, and combinations thereof; and M" is selected from the group consisting of, trivalent transition metals, and combinations thereof. According to an embodiment, M' may be selected from Mg, Ca, Sr, Ba, and mixtures thereof. According to an embodiment, M" may be selected from Mn, Fe, Co, Cu, V, Nb, Ta, Cr, Mo, W, and mixtures thereof. According to an embodiment, the compound that satisfies the formula $M_3BO_5$ may be selected from the ludwigite class minerals, and combinations thereof. The ludwigite class mineral may be selected from pinakiolite, orthopinakiolite, takeuchiite, fredrikssonite, and combinations thereof. The at least one oxygen transfer agent ii) may further comprises a magnesia-phosphate cement that satisfies the formula: $MgM'''PO_4 \cdot mH_2O$; wherein M''' is selected from sodium, lithium, potassium, and mixtures thereof; and m is an integer from 0 to 6. According to an embodiment, the magnesia-phosphate cement may comprise, consist of, or consist essentially of at least one of $MgKPO_4 \cdot mH_2O$ and $MgNaPO_4 \cdot mH_2O$, wherein m is an integer from 0 to 6. According to an embodiment, the metal-boron oxide may comprise, consist of or consist essentially of $Mg_2MnO_2(BO_3)$ and the magnesia-phosphate cement may comprise, consist of, or consist essentially of $NaMg(PO_4) \cdot mH_2O$. According to another embodiment, that at least one oxygen transfer agent ii) may further comprise at least one promotor selected from alkali metals, alkaline earth metals, and mixtures thereof. If present, the at least one promoter may be selected from $Li_2WO_4$, $Na_2WO_4$, $K_2WO_4$, $SrWO_4$, $Li_2MoO_4$, $Na_2MoO_4$, $K_2MoO_4$, $CsMoO4$, $Li_2CO_3$, $Na_2CO_3$, $K_2CO_3$, $CaSO_4$, $Na_2SO_4$, $NaHSO_4$, and mixtures thereof. Suitable such materials are described in U.S. Pat. No. 10,919,027, the contents of which is incorporated by reference herein in its entirety for all purposes.

According to another embodiment, the oxygen transfer agent for converting CO to $CO_2$ may comprise, consist of or consist essentially of at least one reducible metal oxide ii) comprising, consisting of, or consisting essentially of a metal-boron oxide; and a magnesia-phosphate cement. The average oxidation state of the metal in the metal-boron oxide may be from 2.7+ to less than 4.0+, and the oxygen transfer agent may comprise, consist of, or consist essentially of 10% or less of a stoichiometric excess of Mn with respect to the boron. The magnesia-phosphate cement comprises, consists of, or consists essentially of $MgM'''PO_4 \cdot mH_2O$, wherein m is an integer from 0 to 6; and wherein the metal-boron oxide comprises at least one compound that satisfies the formula $M'_2M''BO_5$, wherein M' is selected from one or more of alkaline earth metals, actinide metals, lanthanide metals, and combinations thereof; and M" is selected from one or more of trivalent transition metals. According to an embodiment, the reducible metal oxide ii) may comprise 10 wt % or less of $Mg_6MnO_8$. According to an embodiment, the reducible metal oxide ii) may comprise 5 wt % or less of $Mg_6MnO_8$. The compound that satisfies the formula $M_3BO_5$ may be selected from the ludwigite class minerals, and combinations thereof. These ludwigite class minerals may be selected from pinakiolite, orthopinakiolite, takeuchiite, fredrikssonite, and combinations thereof. According to an embodiment, M' may be selected from Mg, Ca, Sr, Ba, and mixtures thereof and M" may be selected from Mn, Fe, Co, Cu, V, Nb, Ta, Cr, Mo, W, and mixtures thereof. The magnesia-phosphate cement may comprise, consist of, or consist essentially of at least one of $MgKPO_4 \cdot mH_2O$ and $MgNaPO_4 \cdot mH_2O$, wherein m is an integer from 0 to 6. According to an embodiment, the metal-boron oxide comprises $Mg_2MnO_2(BO_3)$. The magnesia-phosphate cement may comprise, consist of, or consist essentially of $NaMg(PO_4) \cdot mH_2O$. According to an embodiment, M''' may be selected from sodium, lithium, potassium, and mixtures thereof. According to an embodiment, the reducible metal oxide ii) may further include at least one promotor selected from alkali metals, alkaline earth metals, and mixtures thereof. The at least one promoter may be selected from $Li_2WO_4$, $Na_2WO_4$, $K_2WO_4$, $SrWO_4$, $Li_2MoO_4$, $Na_2MoO_4$, $K_2MoO_4$, $CsMoO_4$, $Li_2CO_3$, $Na_2CO_3$, $K_2CO_3$, $CaSO_4$, $Na_2SO_4$, $NaHSO_4$, and mixtures thereof. Suitable such oxygen transfer agents are described in detail in U.S. Pat. No. 11,192,092, the entire contents of which is incorporated by reference herein in its entirety for all purposes.

According to an embodiment, the reducible metal oxide ii) used to convert the CO to $CO_2$ may comprise, consist of, or consist essentially of a mixed oxide which is $Mg_6MnO_8$, and at least two promoters which include W and P. The reducible metal oxide ii) of this embodiment may further comprise, consist of, or consist essentially of an alkali metal or compounds thereof. The reducible metal oxide may further include boron or compounds thereof. The reducible metal oxide ii) of this embodiment may further comprise, consist of, or consist essentially of an oxide of an alkaline earth metal. The reducible metal oxide ii) of this embodiment may further include an oxide of manganese, wherein the manganese has a valence state selected from 4+, 3+, 8/3+, and 2+. The reducible metal oxide ii) of this embodiment may further comprise, consist of, or consist essentially of at least one of $NaB_2Mg_4Mn_2O_4$, $NaB_2Mn_2Mg_4O_{11.5}$, $NaMn_2O_4$, $LiMn_2O_4$, $Mg_3Mn_3B_2O_{10}$, $Mg_3(BO_3)_2$, and a non-crystalline compound comprising oxygen and at least one of sodium, boron, magnesium, manganese, and lithium. Details of this embodiment of the reducible metal oxide ii) used as the oxygen transfer agent to convert CO to $CO_2$ may be found in U.S. Pat. No. 10,138,182, the entire disclosure of which is incorporated by reference herein for all purposes.

According to another embodiment, the oxygen transfer agent for converting the CO to $CO_2$ comprises, consists of, or consists essentially of iii) a reducible chalcogen. According to an embodiment, the reducible chalcogen comprises, consists of or consists essentially of:

(A) 10 to 90 wt % $CaSO_4$;
(B) 1 to 85 wt % of a total of W and at least one of Fe and/or Mn; and
(C) 1 to 10 wt % of an alkali metal salt.

According to an embodiment, (B) is W and Fe. According to another embodiment, (B) is W and Mn. According to yet another embodiment, (B) is W, Fe, and Mn. According to an embodiment, (B) may be W and Fe and (C) may be an alkali metal halide. According to another embodiment, (B) may be W and Fe, and (C) may be an alkali metal hydroxide. According to an embodiment, (B) may be W and Mn, and (C) may be an alkali metal halide. According to an embodiment, (B) may be W and Mn, and (C) may be an alkali metal hydroxide. According to an embodiment, (B) may be W, Fe and Mn, and (C) may be an alkali metal halide. According to yet another embodiment, (B) may be W, Fe and Mn, and (C) may be an alkali metal hydroxide. Suitable such materials are described in detail in U.S. Pat. No. 11,104,625, the entire contents of which are incorporated by reference herein in its entirety for all purposes.

According to another embodiment of the invention, the oxygen transfer agent for converting the CO to $CO_2$ may be a reducible metal oxide ii) and a reducible chalcogen iii) and may comprise, consist of, or consist essentially of at least one of a sulfate salt of an alkaline earth metal or a sulfate salt of an alkali metal, and a sulfate salt of manganese. The chalcogen agent iii) has an oxidation state greater than +2. The reducible (oxygen-donating) chalcogen agent iii) and the reducible metal oxide ii) are in solid form. According to an embodiment, the oxygen transfer agent for converting CO to $CO_2$ comprises, consists of or consists essentially of $Mg_6MnO_8$ and at least one promoter selected from Sm, Ga, Ti, W, Mo, V, Nb, Cr, K, Cs, Rb, P, Cu, Pb, Ni and As. According to another this oxygen transfer agent further comprises boron or at least one compound thereof. According to an embodiment, the oxygen transfer agent may additionally comprise at least one alkali metal or a compound thereof. According to another embodiment this the oxygen transfer agent may additionally comprise at least one of an alkali metal oxide or an alkaline earth metal oxide. According to an embodiment, this oxygen transfer agent may comprise a manganese oxide and the manganese may have a valence state of 4+, 3+, 8/3+, or 2+. According to an embodiment, the oxygen transfer agent may comprise, consist of or consist essentially of at least one compound selected from $NaB_2Mg_4Mn_2O_4$, $NaB_2Mn_2Mg_4O_{11.5}$, $NaMn_2O_4$, $LiMn_2O_4$, $Mg_3Mn_3B_2O_{10}$, $Mg_3(BO_3)_2$, and a non-crystalline compound including oxygen and at least one of sodium, boron, magnesium, manganese, or lithium. According to another embodiment, the reducible metal oxide ii) may be ionically and electronically conductive. According to another embodiment, the reducible chalcogen iii) comprises, consists of, or consists essentially of calcium sulfate. According to an embodiment, a chalcogen of the reducible chalcogen iii) has an oxidation state of +3 to +6. According to another embodiment, the reducible chalcogen iii) has an oxidation state greater than +3 and less than +6. According to an embodiment, the chalcogen iii) has an oxidation state of +4. According to another embodiment, this oxygen transfer agent for converting CO to $CO_2$ further comprises, consists of or consists essentially of a sulfate salt of Sm, Ga, Ti, W, Mo, V, Nb, Cr, K, Cs, Rb, P, Cu, Pb, Ni, or As. Details of these embodiments of the oxygen transfer reagent for converting CO to $CO_2$ are described in detail in U.S. Pat. No. 10,968,149, the contents of which is incorporated by reference herein in their entirety for all purposes.

Non-limiting aspects of the invention may be summarized as follows:

Aspect 1: A method of converting CO to $CO_2$ comprising,
a) contacting a first process stream comprising the CO and at least one of C1 to C12 saturated and unsaturated hydrocarbons with an oxygen transfer agent; and
b) oxidizing at least a portion of the CO to $CO_2$ and reducing at least a portion of the oxygen transfer agent to a reduced oxygen transfer agent, at reaction conditions, to provide a second process stream comprising the $CO_2$, the reduced oxygen transfer agent, and the at least one of C1 to C12 saturated and unsaturated hydrocarbons; wherein the C1 to C12 saturated and unsaturated hydrocarbons are not further oxidized; and wherein the oxygen transfer agent comprises at least one of:
i) water; ii) at least one reducible metal oxide; iii) at least one reducible chalcogen; mixtures of any combination of two or more of i), ii), and iii).

Aspect 2: The method of Aspect 1, further comprising, prior to step a), performing a step a1) comprising oxidative coupling of methane or oxidative dehydrogenation of hydrocarbons at hydrocarbon oxidation reaction conditions to produce the first process stream.

Aspect 3: The method of either Aspect 1 or Aspect 2 wherein the oxygen transfer agent comprises i) water and the step a1) produces the water that is used as the oxygen transfer agent in step a).

Aspect 4: The method of any of Aspects 1-3, wherein step a1) and step a) are performed in the same reactor.

5: The method of Aspect 1 or Aspect 2, wherein the oxygen transfer agent comprises ii) or iii) and the same oxygen transfer agent ii) or iii) is used in step a1) and step a).

Aspect 6: The method of Aspect 5, wherein step a1) and step a) are performed in the same reactor.

7. The method of any of Aspects 1-6, wherein the oxygen transfer agent comprises ii) and the at least one reducible metal oxide comprises at least one of alkaline earth metals, actinide metals, lanthanide metals trivalent transition metals, or combinations thereof.

Aspect 8: The method of any of Aspects 1-7, wherein the oxygen transfer agent comprises ii) and the at least one reducible metal oxide comprises at least one of Li/Mn/B/ MgO, Li/Mn/B/$CaSO_4$/MgO, Na/$Pr_6O_{11}$, Mn, Fe, Mo, Ti, V, Pr, Cu, La, Ga, Tb, Nd, Dy, or mixtures or combinations thereof.

Aspect 9: The method of any of Aspects 1-8, wherein the oxygen transfer agent comprises ii) and the reducible metal oxide comprises at least one of $M_3BO_5$, a compound that satisfies the formula $M'_2M''BO_5$, or mixtures thereof; and wherein M is selected from the group consisting of, alkaline earth metals, actinide metals, lanthanide metals, trivalent transition metals, and combinations thereof; M' is selected from the group consisting of, alkaline earth metals, actinide metals, lanthanide metals, and combinations thereof; and M'' is selected from group consisting of, trivalent transition metals, and combinations thereof.

Aspect 10: The method of any of Aspects 1-9, wherein the oxygen transfer agent comprises ii) and the reducible metal oxide comprises a metal-boron oxide; and
a magnesia-phosphate cement;
wherein:
the average oxidation state of the metal in the metal-boron oxide is from 2.7+ to less than 4.0+, and the oxygen transfer agent comprises 10% or less of a stoichiometric excess of Mn with respect to the boron; and
the magnesia-phosphate cement comprises: $MgM'''PO_4 \cdot mH_2O$, wherein m is an integer from 0 to 6; and
wherein the metal-boron oxide comprises at least one compound that satisfies the formula $M'_2M''BO_5$,
wherein M' is selected from one or more of alkaline earth metals, actinide metals, lanthanide metals, and combinations thereof; and M'' is selected from one or more of trivalent transition metals.

Aspect 11: The method of any of Aspects 1-10, wherein the oxygen transfer agent comprises iii) and the reducible chalcogen comprises:
(A) 10 to 90 wt % $CaSO_4$;
(B) 1 to 85 wt % of a total of W and at least one of Fe and/or Mn; and
(C) 1 to 10 wt % of an alkali metal salt.

Aspect 12: The method of any of Aspects 1-11, wherein the oxygen transfer agent comprises ii) and the reducible metal oxide further comprises at least one promotor comprising at least one of alkaline metals, alkaline earth metals, boron, sulfur, salts of tungstic acid, salts of halides, or mixtures thereof.

Aspect 13: The method of any of Aspects 1-12, wherein the step a) takes place in the presence of less than 5 wt % of $O_2$ with respect to the total amount of CO in the first process stream.

Aspect 14: The method of any of Aspects 1-13, wherein the oxygen transfer agent comprises ii) or iii) and the method further comprises a step c) contacting the reduced oxygen transfer agent with a third process stream comprising molecular oxygen to provide a regenerated oxygen transfer agent.

Aspect 15: The method of any of Aspects 1-14, wherein the method further comprises a step d) feeding the regenerated oxygen transfer agent to step a) as the oxygen transfer agent.

Aspect 16: The method of any of Aspects 1-15, wherein the oxygen transfer agent comprises ii) or iii) and the method further comprises a step c) contacting the reduced oxygen transfer agent with a third process stream comprising molecular oxygen to provide a regenerated oxygen transfer agent.

Aspect 17: The method of Aspect any of Aspects 1-16, wherein the method further comprises a step d) feeding the regenerated oxygen transfer agent to step a) and/or to step a1) as the oxygen transfer agent.

Aspect 18: The method of any of Aspects 1-17, wherein the method further comprises a step e) removing at least a portion of the $CO_2$ from the second process stream.

Aspect 19: The method of any of Aspects 1-19, wherein the oxygen transfer agent comprises i) water and the reduced oxygen transfer agent comprises $H_2$.

Aspect 20: A system for oxidatively converting CO to $CO_2$ comprising:
at least one reactor configured for:
a) contacting a first process stream comprising the CO and at least one of C1 to C12 saturated and unsaturated hydrocarbons with an oxygen transfer agent; and
b) oxidizing at least a portion of the CO to $CO_2$, at reaction conditions, and reducing at least a portion of the oxygen transfer agent to provide a second process stream comprising the $CO_2$, the reduced oxygen transfer agent, and the at least one of C1 to C12 saturated and unsaturated hydrocarbons; wherein the at least one of C1 to C12 saturated and unsaturated hydrocarbons are not further oxidized; and
wherein the oxygen transfer agent comprises at least one of:
i) water; ii) at least one reducible metal oxide; iii) at least one reducible chalcogen;
any combination of two or more of i), ii), and iii).

Aspect 21: The system of Aspect 20, wherein the first process stream is produced by a step a1) comprising oxidative coupling of methane or oxidative dehydrogenation of hydrocarbons at hydrocarbon oxidation reaction conditions.

Aspect 22: The system of Aspect 20 or Aspect 21, wherein the oxygen transfer agent comprises i) water and the step a1) produces water that is used as the oxygen transfer agent in step a).

Aspect 23: The system of Aspect 21 or Aspect 22, wherein step a1) and step a) are performed sequentially in the same reactor.

Aspect 24: The system of any of Aspects 21-23, wherein the oxygen transfer agent comprises ii) or iii) and the step a1) utilizes the same oxygen transfer agent ii) as step a).

Aspect 25: The system of Aspect 24, wherein step a1) and step a) are performed sequentially in the same reactor.

Aspect 26: The system of any of Aspects 20-25, wherein the oxygen transfer agent comprises ii) or iii) and the at least one reactor comprises an inlet and an outlet, and wherein the system further comprises a regeneration unit in communication with the inlet and the outlet, wherein the regeneration unit is constructed and arranged to:
c) receive at least a portion of the reduced oxygen transfer agent from the outlet;
d) contact the at least a portion of the reduced oxygen transfer agent with a gas comprising molecular oxygen to produce a regenerated oxygen transfer agent; and
e) feed the regenerated oxygen transfer agent to the inlet.

Aspect 27: The system of any of Aspects 20-26, wherein the system further comprises a purification unit in communication with the at least one reactor, wherein the purification unit is constructed and arranged to remove at least a portion of the $CO_2$ from the second process stream.

28: The system of any of Aspects 20-27, wherein the oxygen transfer agent comprises ii) and the at least one reducible metal oxide comprises at least one of alkaline earth metals, actinide metals, lanthanide metals trivalent transition metals, or combinations thereof.

Aspect 29: The system of any of Aspects 20-28, wherein the oxygen transfer agent comprises ii) and the at least one reducible metal oxide comprises at least one of Li/Mn/B/MgO, Li/Mn/B/$CaSO_4$/MgO, Na/$Pr_6O_{11}$, Mn, Fe, Mo, Ti, V, Pr, Cu, La, Ga, Tb, Nd, Dy, or mixtures or combinations thereof.

30: The system of Aspect any of Aspects 20-29, wherein the oxygen transfer agent comprises ii) and the reducible metal oxide comprises at least one of $M_3BO_5$, a compound that satisfies the formula $M'_2M''BO_5$, or mixtures thereof; and wherein M is selected from the group consisting of, alkaline earth metals, actinide metals, lanthanide metals, trivalent transition metals, and combinations thereof; M' is selected from the group consisting of, alkaline earth metals, actinide metals, lanthanide metals, and combinations thereof; and M'' is selected from group consisting of, trivalent transition metals, and combinations thereof.

31: The system of any of Aspects 20-30, wherein the oxygen transfer agent comprises ii) and the reducible metal oxide comprises a metal-boron oxide; and
a magnesia-phosphate cement;
wherein:
the average oxidation state of the metal in the metal-boron oxide is from 2.7+ to less than 4.0+, and the oxygen transfer agent comprises 10% or less of a stoichiometric excess of Mn with respect to the boron; and
the magnesia-phosphate cement comprises: MgM'''$PO_4$·m$H_2O$, wherein m is an integer from 0 to 6; and
wherein the metal-boron oxide comprises at least one compound that satisfies the formula $M'_2M''BO_5$,
wherein M' is selected from one or more of alkaline earth metals, actinide metals, lanthanide metals, and combinations thereof; and M'' is selected from one or more of trivalent transition metals.

Aspect 32: The system of any of Aspects 20-31, wherein the oxygen transfer agent comprises iii) and the reducible chalcogen comprises:
(A) 10 to 90 wt % $CaSO_4$;
(B) 1 to 85 wt % of a total of W and at least one of Fe and/or Mn; and
(C) 1 to 10 wt % of an alkali metal salt.

Aspect 33: The system of any of Aspects 20-32, wherein the oxygen transfer agent comprises ii) and the reducible metal oxide further comprises at least one promotor comprising at least one of alkaline metals, alkaline earth metals, boron, sulfur, salts of tungstic acid, salts of halides, or mixtures thereof.

Aspect 34: The system of any of Aspects 20-33, wherein the oxygen transfer agent comprises i) water and the reduced oxygen transfer agent comprises $H_2$.

Aspect 35: A method of converting CO to $CH_4$ comprising:
a) contacting a first process stream comprising the CO and at least one C1 to C12 saturated and unsaturated hydrocarbons with a hydrogenation catalyst and a source of $H_2$; and
b) reacting at least a portion of the CO with the $H_2$, at reaction conditions, to provide a second process stream comprising the $CH_4$ and water;
wherein the at least one of C1 to C12 unsaturated hydrocarbons are not reduced in step b); and
wherein the first process stream comprising the CO is a hydrocarbon product stream resulting from the oxidative coupling of methane or oxidative dehydrogenation of hydrocarbons.

Aspect 36: A system for converting CO to $CH_4$ comprising:
  at least one reactor configured for:
  a) contacting a first process stream comprising the CO and at least one C1 to C12 saturated and unsaturated hydrocarbons with a hydrogenation catalyst and a source of $H_2$; and
  b) reacting at least a portion of the CO with the $H_2$, at reaction conditions, to provide a second process stream comprising the $CH_4$ and water;
  wherein the at least one of C1 to C12 unsaturated hydrocarbons are not reduced in step b); and
  wherein the first process stream comprising the CO is a hydrocarbon product stream resulting from the oxidative coupling of methane or oxidative dehydrogenation of hydrocarbons.

EXAMPLES

The following non-limiting example is provided for the purpose of elucidating the advantages obtained from aspects of the present invention and are not intended to limit the invention to only these exemplary embodiments.

Example 1

Mass flow simulations were performed using ChemCAD version 7.1.6 12867 to model the conversion of the CO to $CO_2$ in a typical ODH production stream via a catalytic steam reforming reactor placed downstream of the ODH reactor. The process modeled is shown in FIG. 3 and the results of the steam reforming and $CO_2$ removal are shown in Tables 2-8. The results shown used the built-in water gas shift model option in ChemCAD and also used a stoichiometric model for the OHD reaction in the ODH reactor, using experimentally determined conversions as indicated in the tables.

This system may convert from 1 to 100% of the CO per pass to $CO_2$ on a mass basis and may result in the removal of at least 70%, or at least 71, 72, 73, 74, 75, 76, 77, 78, 79, 80, 81, 82, 83, 84, 85, 86, 87, 88, 89, 90, 91, 92, 93, 94, 95, 96, 97, 98, or at least 99% or up to 100% of all carbon oxide byproducts from the desired ODH olefin product mixture, on a mass basis, performing multiple passes if necessary.

TABLE 2

Compositions of Streams 10 and 20 in FIG. 3

| | Stream 10 Ethane Feed | | | | Stream 20 Reactor Feed | | | |
|---|---|---|---|---|---|---|---|---|
| | kg/hr | wt % | mol/hr | mol % | kg/hr | wt % | mol/hr | mol % |
| Hydrogen | | | | | | | | |
| Methane | 0 | 0.00% | 0 | 0.00% | 0 | 0.00% | 0 | |
| Acetylene | | | | | | | | |
| Ethylene | | | | | | | | |
| Ethane | 142,435 | 100.00% | 4737 | 100.00% | 215,965 | 100.00% | 7182 | |
| Propylene | | | | | | | | |
| Propane | 0 | 0.00% | 0 | 0.00% | 0 | 0.00% | 0 | |
| Butadiene | | | | | | | | |
| Butene | | | | | | | | |
| Butane | | | | | | | | |
| Pentane | | | | | | | | |
| Benzene | | | | | | | | |
| Toluene | | | | | | | | |
| CO | | | | | | | | |
| $CO_2$ | | | | | | | | |
| Water | | | | | | | | |
| Total | 142,435 | | 4737 | | 215965 | | 7182 | |

TABLE 3

Compositions of Streams 30 and 35 in FIG. 3

| | Stream 30 Reactor Product | | | | Stream 35 Water | | | |
|---|---|---|---|---|---|---|---|---|
| | kg/hr | wt % | mol/hr | mol % | kg/hr | wt % | mol/hr | mol % |
| Hydrogen | 3795 | 1.44% | 1882 | 15.90% | | | | |
| Methane | 7605 | 2.89% | 474 | 4.00% | | | | |
| Acetylene | 935 | 0.36% | 36 | 0.30% | | | | |
| Ethylene | 113,034 | 43.00% | 4029 | 34.02% | | | | |
| Ethane | 73,644 | 28.02% | 2449 | 20.68% | | | | |
| Propylene | 2418 | 0.92% | 57 | 0.49% | | | | |
| Propane | 211 | 0.08% | 5 | 0.04% | | | | |
| Butadiene | 4079 | 1.55% | 75 | 0.64% | | | | |
| Butene | 403 | 0.15% | 7 | 0.06% | | | | |
| Butane | 417 | 0.16% | 7 | 0.06% | | | | |
| Pentane | 1244 | 0.47% | 17 | 0.15% | | | | |
| Benzene | 935 | 0.36% | 12 | 0.10% | | | | |

TABLE 3-continued

Compositions of Streams 30 and 35 in FIG. 3

| | Stream 30 Reactor Product | | | | Stream 35 Water | | | |
|---|---|---|---|---|---|---|---|---|
| | kg/hr | wt % | mol/hr | mol % | kg/hr | wt % | mol/hr | mol % |
| Toluene | 189 | 0.07% | 2 | 0.02% | | | | |
| CO | 7 | 0.00% | 0 | 0.00% | | | | |
| $CO_2$ | 6310 | 2.40% | 143 | 1.21% | | | | |
| Water | 47,643 | 18.12% | 2645 | 22.33% | 47,643 | | 2645 | |
| Total | 262,869 | | 11,842 | | 47,643 | | 2645 | |

TABLE 4

Compositions of Streams 36 and 40 in FIG. 3

| | Stream 36 COx | | | | Stream 40 Demethanizer Feed | | | |
|---|---|---|---|---|---|---|---|---|
| | kg/hr | wt % | mol/hr | mol % | kg/hr | wt % | mol/hr | mol % |
| Hydrogen | | | | | 3722 | 1.78% | 1846 | 20.47% |
| Methane | | | | | 7605 | 3.64% | 474 | 5.26% |
| Acetylene | | | | | 0 | 0.00% | 0 | 0.00% |
| Ethylene | | | | | 114,041 | 54.59% | 4065 | 45.08% |
| Ethane | | | | | 73,644 | 35.25% | 2449 | 27.16% |
| Propylene | | | | | 2418 | 1.16% | 57 | 0.64% |
| Propane | | | | | 211 | 0.10% | 5 | 0.05% |
| Butadiene | | | | | 4079 | 1.95% | 75 | 0.84% |
| Butene | | | | | 403 | 0.19% | 7 | 0.08% |
| Butane | | | | | 417 | 0.20% | 7 | 0.08% |
| Pentane | | | | | 1244 | 0.60% | 17 | 0.19% |
| Benzene | | | | | 935 | 0.45% | 12 | 0.13% |
| Toluene | | | | | 189 | 0.09% | 2 | 0.02% |
| CO | 7 | 0.12% | 0 | 0.18% | 0 | 0.00% | 0 | 0.00% |
| $CO_2$ | 6310 | 99.88% | 143 | 99.82% | 0 | 0.00% | 0 | 0.00% |
| Water | | | | | 0 | 0.00% | 0 | 0.00% |
| Total | 6318 | | 144 | | 208,908 | | 9018.1 | |

40

TABLE 5

Compositions of Streams 45 and 46 in FIG. 3

| | Stream 45 Hydrogen | | | | Stream 46 Fuel Gas | | | |
|---|---|---|---|---|---|---|---|---|
| | kg/hr | wt % | mol/hr | mol % | kg/hr | wt % | mol/hr | mol % |
| Hydrogen | 3350 | 53% | 1662 | 90% | 372 | | 185 | |
| Methane | 2962 | 47% | 185 | 10% | 4643 | | 289 | |
| Acetylene | | | | | | | | |
| Ethylene | | | | | | | | |
| Ethane | | | | | | | | |
| Propylene | | | | | | | | |
| Propane | | | | | | | | |
| Butadiene | | | | | | | | |
| Butene | | | | | | | | |
| Butane | | | | | | | | |
| Pentane | | | | | | | | |
| Benzene | | | | | | | | |
| Toluene | | | | | | | | |
| CO | | | | | | | | |
| $CO_2$ | | | | | | | | |
| Water | | | | | | | | |
| Total | 6312 | | 1846 | | 5015 | | 474 | |

TABLE 6

Compositions of Streams 50 and 55 in FIG. 3

| | Stream 50 De-ethanizer Feed | | | | Stream 55 C3+ Stream | | | |
|---|---|---|---|---|---|---|---|---|
| | kg/hr | wt % | mol/hr | mol % | kg/hr | wt % | mol/hr | mol % |
| Hydrogen | | | | | | | | |
| Methane | | | | | | | | |
| Acetylene | | | | | | | | |
| Ethylene | 114,041 | 58% | 4065 | 61% | | | | |
| Ethane | 73,644 | 37% | 2449 | 37% | | | | |
| Propylene | 2418 | 1% | 57 | 1% | 2418 | 24% | 57 | 31% |
| Propane | 211 | 0% | 5 | 0% | 211 | 2% | 5 | 3% |
| Butadiene | 4079 | 2% | 75 | 1% | 4079 | 41% | 75 | 41% |
| Butene | 403 | 0% | 7 | 0% | 403 | 4% | 7 | 4% |
| Butane | 417 | 0% | 7 | 0% | 417 | 4% | 7 | 4% |
| Pentane | 1244 | 1% | 17 | 0% | 1244 | 13% | 17 | 9% |
| Benzene | 935 | 0% | 12 | 0% | 935 | 9% | 12 | 7% |
| Toluene | 189 | 0% | 2 | 0% | 189 | 2% | 2 | 1% |
| CO | | | | | | | | |
| $CO_2$ | | | | | | | | |
| Water | | | | | | | | |
| Total | 197,581 | | 6698 | | 9896 | | 183 | |

TABLE 7

Compositions of Streams 60 and 70 in FIG. 3

| | Stream 60 C2 Splitter Feed | | | | Stream 70 Product Ethylene | | | |
|---|---|---|---|---|---|---|---|---|
| | kg/hr | wt % | mol/hr | mol % | kg/hr | wt % | mol/hr | mol % |
| Hydrogen | | | | | | | | |
| Methane | | | | | | | | |
| Acetylene | | | | | | | | |
| Ethylene | 114,041 | 61% | 4065 | 62% | 114,041 | 99.90% | 4065 | 99.91% |
| Ethane | 73,644 | 39% | 2449 | 38% | 114 | 0.10% | 4 | 0.09% |
| Propylene | | | | | | | | |
| Propane | | | | | | | | |
| Butadiene | | | | | | | | |
| Butene | | | | | | | | |
| Butane | | | | | | | | |
| Pentane | | | | | | | | |
| Benzene | | | | | | | | |
| Toluene | | | | | | | | |
| CO | | | | | | | | |
| CO2 | | | | | | | | |
| Water | | | | | | | | |
| Total | 187,685 | | 6514 | | 114,155 | | 4069 | |

TABLE 8

Composition of Stream 75 in FIG. 3

| | Stream 75 Recycle Ethane | | | |
|---|---|---|---|---|
| | kg/hr | wt % | mol/hr | mol % |
| Hydrogen | | | | |
| Methane | | | | |
| Acetylene | | | | |
| Ethylene | | | | |
| Ethane | 73,530 | | 2445 | |
| Propylene | | | | |
| Propane | | | | |
| Butadiene | | | | |
| Butene | | | | |
| Butane | | | | |
| Pentane | | | | |
| Benzene | | | | |
| Toluene | | | | |
| CO | | | | |
| $CO_2$ | | | | |
| Water | | | | |
| Total | 73,530 | | 2445 | |

Within this specification, embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

In some embodiments, the invention herein can be construed as excluding any element or process step that does not materially affect the basic and novel characteristics of the invention. Additionally, in some embodiments, the invention can be construed as excluding any element or process step not specified herein.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A method of converting CO to $CO_2$ comprising,
    a1) oxidative coupling of methane or oxidative dehydrogenation of hydrocarbons at hydrocarbon oxidation reaction conditions to produce a first process stream comprising the CO and at least one of C1 to C12 saturated or unsaturated hydrocarbons;
    a) contacting the first process stream comprising the CO and the at least one of C1 to C12 saturated or unsaturated hydrocarbons with an oxygen transfer agent; and
    b) oxidizing at least a portion of the CO to $CO_2$ and reducing at least a portion of the oxygen transfer agent to a reduced oxygen transfer agent, at reaction conditions, to provide a second process stream comprising the $CO_2$, the reduced oxygen transfer agent, and the at least one of C1 to C12 saturated or unsaturated hydrocarbons;
    wherein:
    the C1 to C12 saturated or unsaturated hydrocarbons are not further oxidized in step b);
    the hydrocarbon oxidation reaction conditions include the presence of less than 5 wt % of $O_2$ with respect to the total amount of CO in the first process stream; and
    the oxygen transfer agent in step b) comprises water.

2. The method of claim 1 wherein the step a1) produces at least a portion of the water that is used as the oxygen transfer agent in step a).

3. The method of claim 2, wherein step a1) and step a) are performed in the same reactor.

4. The method of claim 1, wherein at least a portion of the water that is used as an oxygen transfer agent is added to step a).

5. The method of claim 1, wherein the first process stream is contacted with a catalyst comprising at least one of iron, zinc, nickel, rhodium, iridium, platinum, palladium, gold, ruthenium, or a combination thereof.

6. The method of claim 1, wherein the method further comprises
    step e) removing at least a portion of the $CO_2$ from the second process stream.

7. The method of claim 1, wherein the reduced oxygen transfer agent comprises $H_2$.

8. A system for oxidatively converting CO to $CO_2$ comprising:
    at least one reactor configured for:
    a1) oxidative coupling of methane or oxidative dehydrogenation of hydrocarbons at hydrocarbon oxidation reaction conditions to produce a first process stream comprising the CO and at least one of C1 to C12 saturated or unsaturated hydrocarbons;
    a) contacting a first process stream comprising the CO and the at least one of C1 to C12 saturated or unsaturated hydrocarbons with an oxygen transfer agent; and
    b) oxidizing at least a portion of the CO to $CO_2$, at reaction conditions, and reducing at least a portion of the oxygen transfer agent to provide a second process stream comprising the $CO_2$, the reduced oxygen transfer agent, and the at least one of C1 to C12 saturated or unsaturated hydrocarbons; wherein:
    the at least one of C1 to C12 saturated or unsaturated hydrocarbons are not further oxidized in step b);
    the hydrocarbon oxidation reaction conditions include the presence of less than 5 wt % of $O_2$ with respect to the total amount of CO in the first process stream; and
    the oxygen transfer agent in step b) comprises water.

9. The system of claim 8, wherein the step a1) produces at least a portion of the water that is used as the oxygen transfer agent in step a).

10. The system of claim 9, wherein step a1) and step a) are performed sequentially in the same reactor.

11. The system of claim 8, wherein at least a portion of the water that is used as an oxygen transfer agent is added to step a).

12. The system of claim 8, wherein the first process stream is contacted with a catalyst comprising at least one of iron, zinc, nickel, rhodium, iridium, platinum, palladium, gold, ruthenium, or a combination thereof.

13. The system of claim 8, wherein the system further comprises a purification unit in communication with the at least one reactor, wherein the purification unit is constructed and arranged to remove at least a portion of the $CO_2$ from the second process stream.

14. The system of claim 8, wherein the reduced oxygen transfer agent comprises $H_2$.

* * * * *